(12) United States Patent
Morita

(10) Patent No.: US 10,856,805 B2
(45) Date of Patent: Dec. 8, 2020

(54) IMAGE PROCESSING DEVICE, LIVING-BODY OBSERVATION DEVICE, AND IMAGE PROCESSING METHOD

(71) Applicant: OLYMPUS CORPORATION, Tokyo (JP)

(72) Inventor: Yasunori Morita, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 489 days.

(21) Appl. No.: 15/680,725

(22) Filed: Aug. 18, 2017

(65) Prior Publication Data

US 2017/0340273 A1 Nov. 30, 2017

Related U.S. Application Data

(63) Continuation of application No. PCT/JP2015/056297, filed on Mar. 4, 2015.

(51) Int. Cl.
*A61B 5/00* (2006.01)
*G06T 7/00* (2017.01)
(Continued)

(52) U.S. Cl.
CPC ........ *A61B 5/4872* (2013.01); *A61B 1/00009* (2013.01); *A61B 1/00096* (2013.01); (Continued)

(58) Field of Classification Search
CPC ... A61B 5/4872; A61B 5/0075; A61B 5/0062; A61B 5/0059; A61B 1/00009; (Continued)

(56) References Cited

U.S. PATENT DOCUMENTS 4,983,019 A 1/1991 Ikuno et al.
4,997,769 A 3/1991 Lundsgaard
(Continued)

FOREIGN PATENT DOCUMENTS

EP 2417897 A1 2/2012
EP 2810596 A1 12/2014
(Continued)

OTHER PUBLICATIONS

International Search Report and Written Opinion dated Apr. 23, 2013 issued in PCT/JP2013/052232.
(Continued)

*Primary Examiner* — Carolyn A Pehlke
(74) *Attorney, Agent, or Firm* — Scully, Scott, Murphy & Presser, P.C.

(57) ABSTRACT

For the purpose of allowing fat to be stably distinguished irrespective of individual differences, so as to prevent damage to nerves that surround a target organ, an image processing device includes: a fat-image-region extracting unit that extracts a fat-image region that indicates a region, in a living-tissue image, where fat exists; a fat-color-component detecting unit that detects a fat-color-component amount that determines the color of fat, from the fat-image region extracted by the fat-image-region extracting unit; and a correction unit that corrects the signal intensity of the fat-image region extracted by the fat-image-region extracting unit on the basis of the fat-color-component amount detected by the fat-color-component detecting unit.

12 Claims, 12 Drawing Sheets

(51) Int. Cl.
- *A61B 1/00* (2006.01)
- *A61B 1/06* (2006.01)
- *G06K 9/20* (2006.01)
- *G06T 7/90* (2017.01)
- *A61B 1/05* (2006.01)
- *A61B 5/145* (2006.01)
- *A61B 5/1455* (2006.01)

(52) U.S. Cl.
CPC ............ *A61B 1/051* (2013.01); *A61B 1/0638* (2013.01); *A61B 1/0646* (2013.01); *A61B 5/0075* (2013.01); *A61B 5/1455* (2013.01); *A61B 5/14546* (2013.01); *A61B 5/489* (2013.01); *A61B 5/742* (2013.01); *G06K 9/2018* (2013.01); *G06K 9/2081* (2013.01); *G06T 7/0012* (2013.01); *G06T 7/0014* (2013.01); *G06T 7/90* (2017.01); *A61B 1/0684* (2013.01); *A61B 5/0084* (2013.01); *G06K 2209/051* (2013.01); *G06T 2200/24* (2013.01); *G06T 2207/10024* (2013.01); *G06T 2207/10068* (2013.01); *G06T 2207/30024* (2013.01); *G06T 2207/30101* (2013.01)

(58) Field of Classification Search
CPC ... A61B 1/00096; A61B 1/051; A61B 1/0638; A61B 1/0646; G06T 7/90; G06T 7/0012; G06T 7/0014
See application file for complete search history.

(56) References Cited

U.S. PATENT DOCUMENTS

| | | |
|---|---|---|
| 6,452,188 B1 | 9/2002 | Chubb |
| 2003/0216795 A1 | 11/2003 | Harth et al. |
| 2007/0038124 A1 | 2/2007 | Fulghum, Jr. et al. |
| 2007/0197884 A1 | 8/2007 | Bornstein |
| 2009/0322863 A1 | 12/2009 | Takahashi |
| 2010/0049058 A1* | 2/2010 | Ishihara ................ A61B 1/043 600/477 |
| 2010/0082019 A1 | 4/2010 | Neev |
| 2011/0254937 A1 | 10/2011 | Yoshino |
| 2011/0270035 A1 | 11/2011 | Gono |
| 2012/0302892 A1 | 11/2012 | Lue et al. |
| 2013/0147400 A1 | 6/2013 | Van Herpen et al. |
| 2014/0301617 A1 | 10/2014 | Shida et al. |
| 2014/0316279 A1 | 10/2014 | Morishita |

FOREIGN PATENT DOCUMENTS

| | | |
|---|---|---|
| JP | H01-217415 A | 8/1989 |
| JP | 2007-282965 A | 11/2007 |
| JP | 2010-115341 A | 5/2010 |
| JP | 2011-218090 A | 11/2011 |
| JP | 2011-224038 A | 11/2011 |
| WO | WO 2010/116902 A1 | 10/2010 |
| WO | WO-2012165505 A1 * | 12/2012 ......... A61B 1/00009 |
| WO | WO-2013035738 A1 * | 3/2013 ............ G01N 21/64 |
| WO | WO 2013/100030 A1 | 7/2013 |
| WO | WO 2013/115323 A1 | 8/2013 |

OTHER PUBLICATIONS

International Search Report dated Jun. 2, 2015 issued in PCT/JP2015/056297.

Extended Supplementary European Search Report dated Jul. 16, 2015 issued in 13744253.9.

United States Office Action dated Apr. 7, 2017 issued in U.S. Appl. No. 14/321,978.

Office Action dated Oct. 19, 2017 received in U.S. Appl. No. 14/321,978.

Office Action dated Mar. 7, 2018 received in U.S. Appl. No. 14/321,978.

* cited by examiner

IMAGE PROCESSING DEVICE, LIVING-BODY OBSERVATION DEVICE, AND IMAGE PROCESSING METHOD

CROSS-REFERENCE TO RELATED APPLICATIONS

This application is a Continuation Application of International Application No. PCT/JP2015/056297 filed on Mar. 4, 2015. The content of International Application No. PCT/JP2015/056297 is hereby incorporated herein by reference in their entirety.

TECHNICAL FIELD

The present invention relates to an image processing device, a living-body observation device, and an image processing method.

BACKGROUND ART

There is known narrow-band light observation (NBI) in which illumination light having a wavelength in a narrowed band that is likely to be absorbed by hemoglobin contained in blood is radiated to highlight capillary blood vessels etc. on a mucosal surface (for example, see PTL 1).

This narrow-band light observation is expected to be an alternative observation method to dye spraying, which is widely performed for detailed diagnosis of the esophagus area and observation of large-intestine pit patterns (gland-duct structure), and is expected to contribute to the efficiency of examination due to a reduction in examination time and in unnecessary biopsies.

However, in the narrow-band light observation, although blood vessels can be highlighted, it is difficult to highlight nerves.

For example, in a case in which nerves are preserved in surgery to remove the entire rectum or in surgery to remove all of the prostate, when the target organ is removed, it is necessary to expose and remove the target organ so as not to damage the nerves that are distributed so as to surround the target organ. However, because thin nerves having diameters from 50 μm to 300 μm are white or transparent, it is difficult to observe them even through magnified observation using a laparoscope. Thus, there is a disadvantage that doctors have no choice but to perform surgeries while relying on their experience and intuition, and there is a high possibility that nerves are damaged.

In order to overcome this disadvantage, a living-body observation device that clarifies the structure of tissue on the surface of a target organ, such as a target to be removed, so as to prevent damage to nerves that surround the target organ, has been proposed (for example, see PTL 2). In PTL 2, the existence of nerves that surround a target organ in a fat layer is considered, and, because β-carotene contained in fat and hemoglobin contained in blood have absorption characteristics in different wavelength bands, irradiation light in the corresponding wavelength band is radiated to acquire an image in which fat can be easily distinguished, thus making it possible to perform surgery so as not to damage nerves that are distributed in the fat layer.

CITATION LIST

Patent Literature

{PTL 1} Japanese Unexamined Patent Application, Publication No. 2011-224038
{PTL 2} PCT International Publication No. WO 2013/115323 Pamphlet

SUMMARY OF INVENTION

An aspect of the present invention is an image processing device including: a fat-image-region extracting unit that extracts a fat-image region that is a region where fat exists in a living-tissue image; a fat-color-component detecting unit that detects a fat-color-component amount that determines a color of fat, from the fat-image region extracted by the fat-image-region extracting unit; and a correction unit that corrects intensity of signals of the fat-image region extracted by the fat-image-region extracting unit, on the basis of the fat-color-component amount detected by the fat-color-component detecting unit.

Furthermore, according to another aspect, the present invention provides an image processing device including: a fat-image-region extracting unit that extracts a fat-image region that is a region where fat exists in a living-tissue image; an exposed-fat-region specifying unit that allows an operator to specify an exposed-fat region, in the living-tissue image, where fat is exposed without being covered with another tissue; a fat-color-component detecting unit that detects a fat-color-component amount that determines a color of fat, from the exposed-fat region specified through the exposed-fat-region specifying unit; and a correction unit that corrects intensity of signals of the fat-image region extracted by the fat-image-region extracting unit, on the basis of the fat-color-component amount detected by the fat-color-component detecting unit.

Furthermore, another aspect of the present invention is a living-body observation device including: a radiation unit that radiates illumination light onto living tissue; an image acquisition unit that acquires a living-tissue image by capturing, within reflected light reflected at the living tissue onto which the illumination light has been radiated by the radiation unit, reflected light in a wavelength band in which absorption characteristics of β-carotene are higher than absorption characteristics of hemoglobin; the above-described image processing device that processes the living-tissue image acquired by the image acquisition unit; and a display unit that displays an image generated by the fat highlighting unit.

Furthermore, another aspect of the present invention is a living-body observation device including: a radiation unit that radiates illumination light onto living tissue; an image acquisition unit that acquires a living-tissue image by capturing reflected light reflected at the living tissue onto which the illumination light has been radiated by the radiation unit; and the above-described image processing device.

Furthermore, another aspect of the present invention is a fat-image-region extracting step of extracting a fat-image region that is a region where fat exists in a living-tissue image; a fat-color-component detecting step of detecting a fat-color-component amount that determines a color of fat, from the fat-image region extracted in the fat-image-region extracting step; and a correcting step of correcting intensity of signals of the fat-image region extracted in the fat-image-region extracting step, on the basis of the fat-color-component amount detected in the fat-color-component detecting step.

DESCRIPTION OF EMBODIMENTS

An image processing device (image processing unit) 16 and a living-body observation device 1 that is provided with the same, according to a first embodiment of the present invention, will be described below with reference to the drawings.

Figure 1:
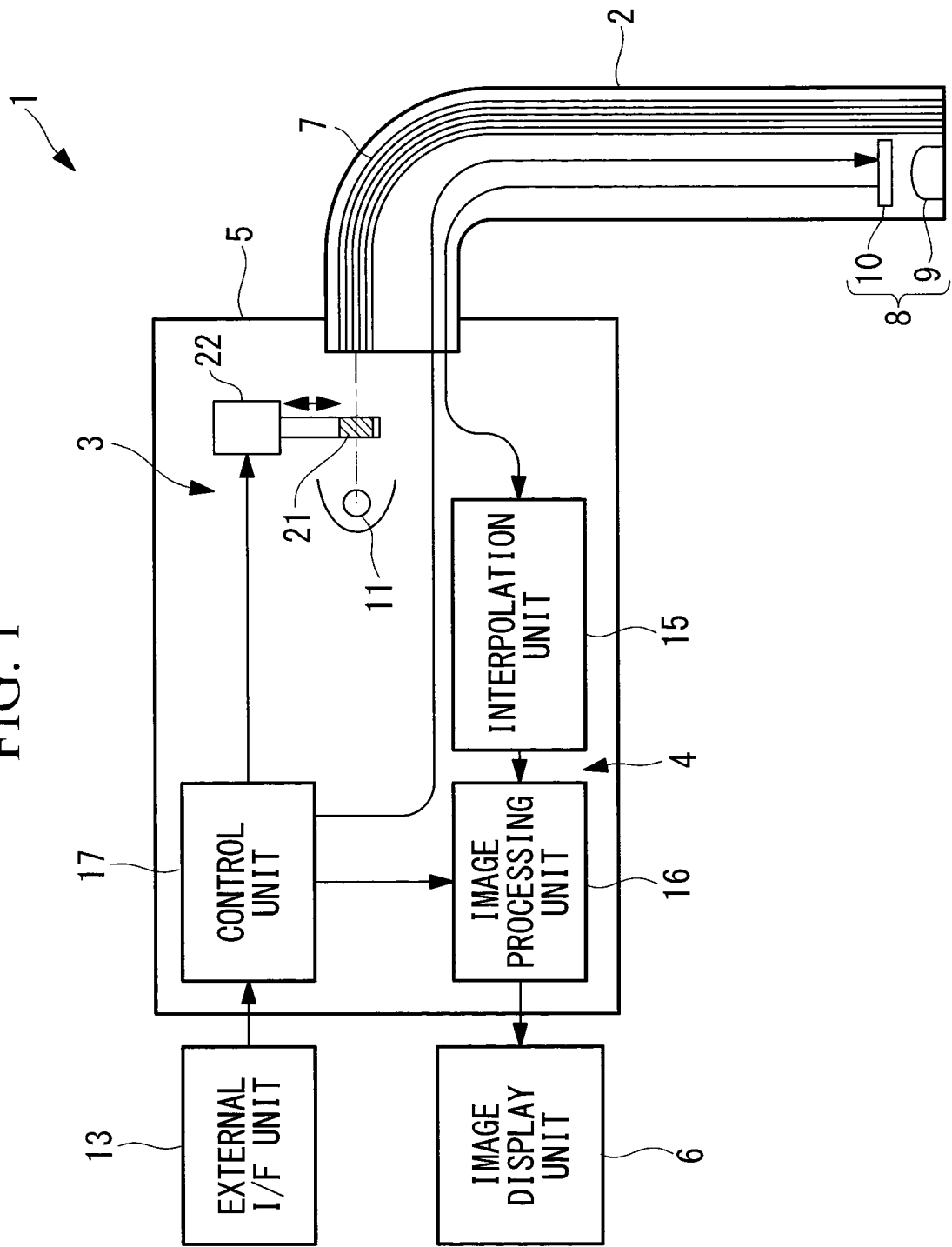
FIG. 1 is a schematic view showing the overall configuration of a living-body observation device according to a first embodiment of the present invention.

First, the living-body observation device 1 of this embodiment is an endoscope and, as shown in FIG. 1, is provided with: an insertion portion 2 that is inserted into a living body; a main unit 5 that is connected to the insertion portion 2 and that includes a light source unit (radiation unit) 3 and a signal processing unit 4; an image display unit (display unit) 6 that displays an image generated by the signal processing unit 4; and an external I/F unit 13.

The insertion portion 2 is provided with: an illumination-light optical system 7 that radiates light input from the light source unit 3 toward a subject; and a capturing optical system (image acquisition unit) 8 that captures reflected light coming from the subject. The illumination-light optical system 7 is a light-guide cable that is disposed over the entire length in the longitudinal direction of the insertion portion 2 and that guides light entering from the light source unit 3, which is provided close to a proximal end thereof, toward a distal end thereof.

The capturing optical system 8 is provided with: an objective lens 9 that collects reflected light, coming from a subject, of the light irradiated by the illumination-light optical system 7; and an image acquisition device 10 that captures the light collected by the objective lens 9.

The image acquisition device 10 is a color CCD, for example.

The light source unit 3 is provided with: a xenon lamp 11 that emits white light in a wide wavelength band; a short-wavelength cut filter 21 that can be inserted on or removed from the optical axis of light emitted from the xenon lamp 11 in order to cut out light having predetermined wavelengths from the white light emitted from the xenon lamp 11; and a linear motion mechanism 22 that is controlled by a control unit 17, which will be described later, to insert or remove the short-wavelength cut filter 21 on or from the optical axis.

Figure 2A:
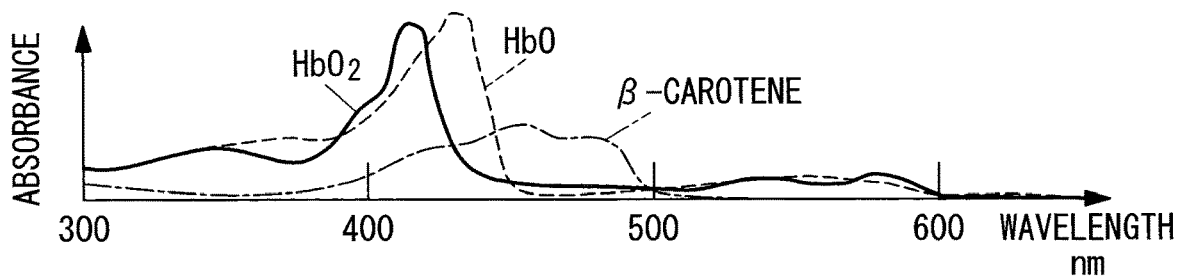
FIG. 2A is a view showing absorption characteristics of β-carotene and absorption characteristics of hemoglobin.
Figure 2B:
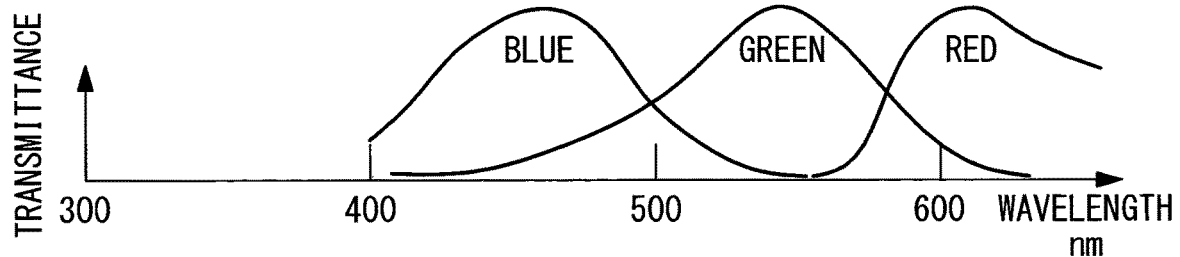
FIG. 2B is a view showing transmittance characteristics of color filters that are provided in a color CCD of the living-body observation device shown in FIG. 1.
Figure 2C:
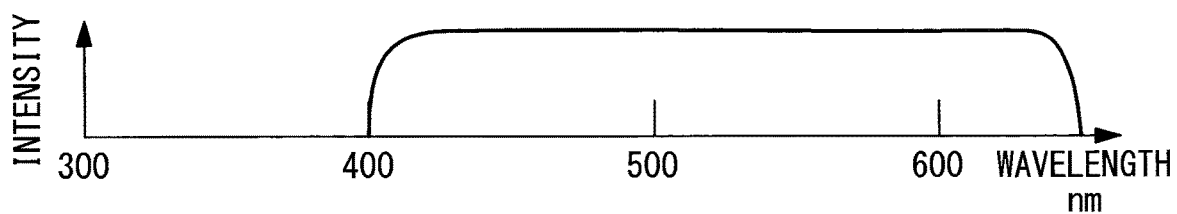
FIG. 2C is a view showing light-intensity characteristics of a xenon lamp of the living-body observation device shown in FIG. 1.
Figure 2D:
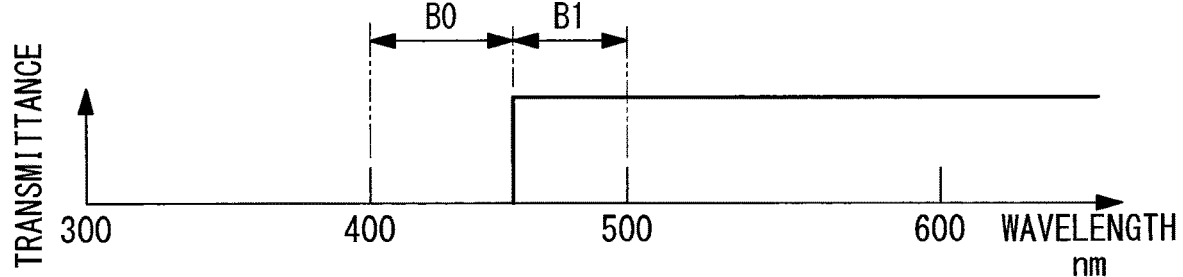
FIG. 2D is a view showing transmittance characteristics of a filter used in a special-light observation mode in the living-body observation device shown in FIG. 1.

As shown in FIG. 2D, the short-wavelength cut filter 21 blocks light in a wavelength band shorter than 450 nm and transmits light in a wavelength band equal to or longer than 450 nm.

As shown in FIG. 2B, the image acquisition device 10 is provided with color filters (not shown) that have transmittances for respective colors.

Figure 12A:
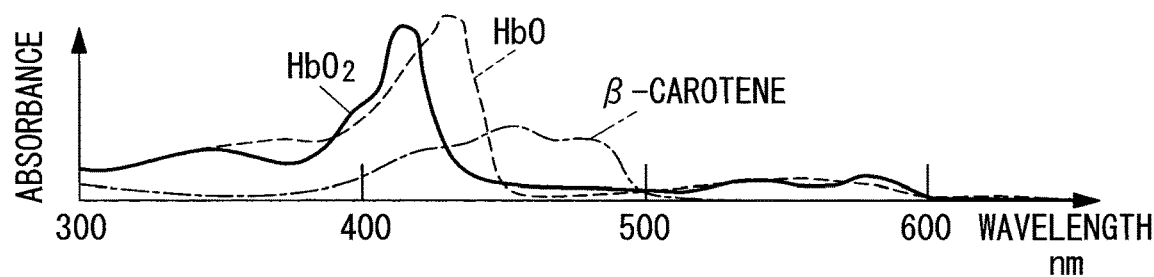
FIG. 12A is a view showing absorption characteristics of β-carotene and absorption characteristics of hemoglobin.
Figure 12B:
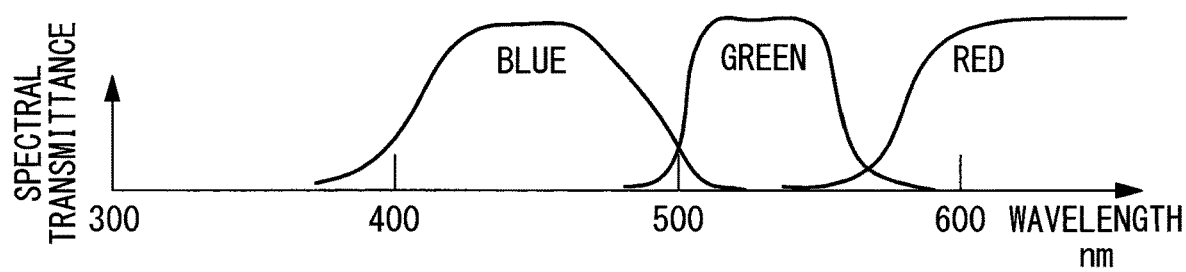
FIG. 12B is a view showing spectral transmittance characteristics of a color-separation prism in the living-body observation device shown in FIG. 11.
Figure 12C:
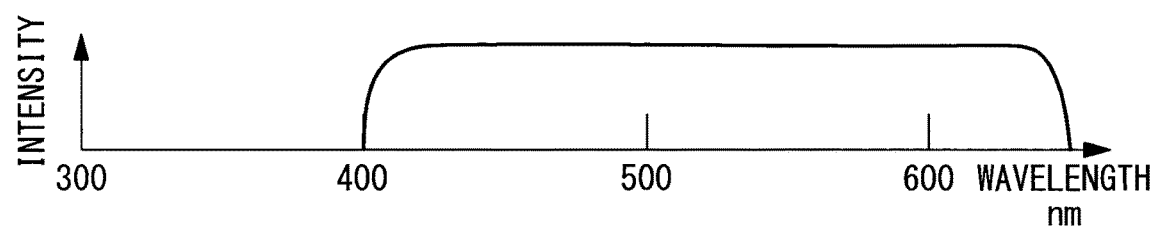
FIG. 12C is a view showing light-intensity characteristics of a xenon lamp in the living-body observation device shown in FIG. 11.

Furthermore, the xenon lamp 11 has an intensity spectrum, as shown in FIGS. 2C and 12C.

Here, as shown in FIGS. 2A, 8A, 10A, and 12A, β-carotene contained in living tissue has high absorption characteristics in the region from 400 nm to 500 nm. Furthermore, hemoglobin ($HbO_2$, HbO), which is a component in blood, has high absorption characteristics in a wavelength band equal to or shorter than 450 nm and in a wavelength band from 500 nm to 600 nm.

Specifically, a blue wavelength band of the color filters of the image acquisition device 10 includes: a wavelength band in which absorption by hemoglobin is larger than absorption by β-carotene; and a wavelength band in which absorption by β-carotene is larger than absorption by hemoglobin. Then, the short-wavelength cut filter 21 is inserted on the optical axis, thereby transmitting therethrough, in the blue wavelength band, only light in the wavelength band in which absorption by β-carotene is larger than absorption by hemoglobin, thus radiating the light therein onto the subject.

Then, an image acquired by radiating the light therein is less affected by absorption by blood vessels (hemoglobin) and has much absorption by fat tissue (β-carotene). On the other hand, when the short-wavelength cut filter 21 is removed from the optical axis, because light in the entire blue wavelength band is radiated onto the subject, a white-light image can be acquired, using light of red and green radiated at the same time.

Furthermore, in a green wavelength band, there is no absorption by β-carotene, and there is absorption by hemoglobin; thus, in an image acquired by radiating light therein, a low-intensity region indicates a region where blood exists, for example, a blood vessel.

Furthermore, in a red wavelength band, because there is no absorption by β-carotene or absorption by hemoglobin, an image acquired by radiating light therein shows morphological characteristics of the living-tissue surface.

The signal processing unit 4 is provided with: an interpolation unit 15 that processes image signals acquired by the image acquisition device 10; and the image processing unit (image processing device) 16 which processes the image signals processed by the interpolation unit 15. Furthermore, the signal processing unit 4 is provided with the control unit 17. The control unit 17 synchronizes, on the basis of an instruction signal sent from the external I/F unit 13, the timing of capturing performed by the image acquisition device 10, the insertion/removal of the short-wavelength cut filter 21, and the timing of image processing performed by the image processing unit 16.

The interpolation unit 15 applies known demosaicing processing to color images that are acquired by pixels corresponding to the respective colors of the image acquisition device 10, thus obtaining three-channel image signals.

Figure 3:
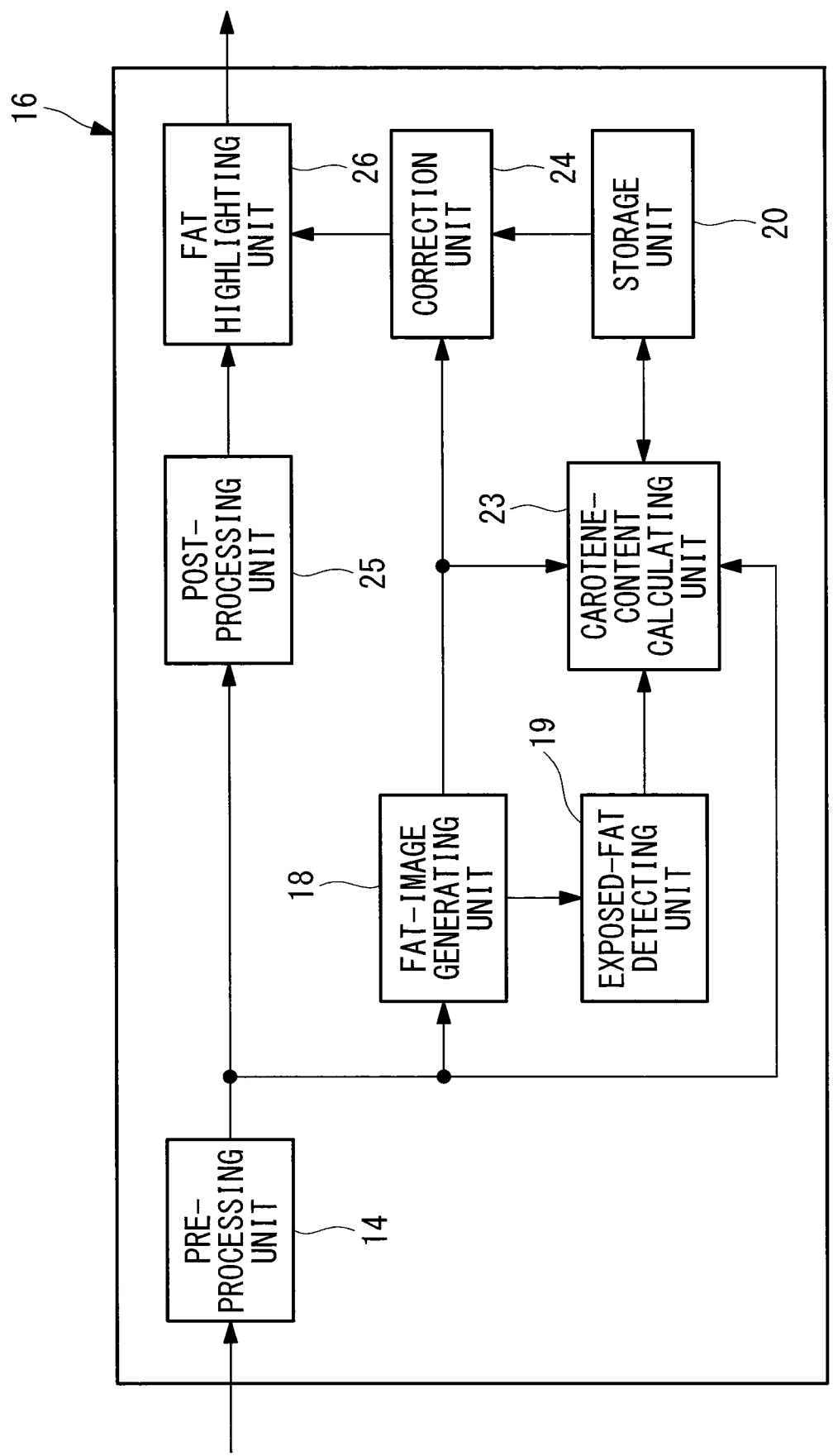
FIG. 3 is a block diagram showing an image processing device that is provided in the living-body observation device shown in FIG. 1.

As shown in FIG. 3, the image processing unit 16 is provided with: a pre-processing unit 14; a fat-image generating unit (fat-image-region extracting unit) 18; an exposed-fat detecting unit 19; a storage unit 20; a carotene-content calculating unit (fat-color-component detecting unit) 23; a correction unit 24; a post-processing unit 25; and a fat highlighting unit 26.

The pre-processing unit 14 performs, on the three-channel image signals, which are input from the interpolation unit 15, OB (Optical Black) clamp processing, gain correction processing, and WB (White Balance) correction processing by using an OB clamp value, a gain correction value, and a WB coefficient value that are stored in advance in the control unit 17.

The fat-image generating unit 18 generates a fat image signal on the basis of the image signals processed by the pre-processing unit 14. The image signals contain image signals with respect to three types of illumination light, i.e., illumination light of blue, green, and red. The fat-image generating unit 18 generates a one-channel fat image signal from the three-channel image signals. The fat image signal is a signal that has a higher signal value as the β-carotene content contained in the subject is higher.

The exposed-fat detecting unit 19 detects an exposed-fat region from the fat image signal sent from the fat-image generating unit 18. Here, exposed fat means fat in a state in which it is not covered with blood (hemoglobin) or living tissue (fascia). As a method for detecting an exposed-fat region, pixels having signal values that exceed a reference value set in advance are detected as an exposed-fat region.

Specifically, the exposed-fat detecting unit 19 detects the maximum value from the fat image signal. The detected maximum value is compared with an exposed-fat value stored in advance in an internal memory (not shown). As a result of the comparison, if the maximum value is larger than the exposed-fat value, the exposed-fat value in the internal memory is updated to be the detected maximum value, and the detected maximum value is stored therein. Next, the exposed-fat detecting unit 19 detects, from the fat image signal, pixels having signal values that are larger than the reference value, as an exposed-fat region, the reference value being obtained by subtracting a predetermined threshold from the exposed-fat value, and outputs the coordinates thereof.

Here, the exposed-fat detection processing is performed when an ON/OFF instruction signal for the detection processing is input from the external I/F unit 13, to be described later, via the control unit 17. The exposed-fat detection processing is performed when the ON/OFF instruction signal is set to ON, and the exposed-fat detecting unit 19 does not perform the detection processing when the ON/OFF instruction signal is set to OFF.

The storage unit 20 stores the carotene content in exposed fat. The storage unit 20 stores, as an initial value, a known carotene content that is stored in advance in the control unit 17. The known carotene content may be an average carotene content in fat or may be read from a patient information database on the server.

The carotene-content calculating unit 23 first calculates the average value of the fat image signal at the coordinates of the pixels, which are detected as an exposed-fat region, sent from the exposed-fat detecting unit 19. Here, only proper-exposure pixels are used as pixels from which the average value is calculated. Specifically, the carotene-content calculating unit 23 calculates luminance signals from the image signals obtained after the image processing performed by the pre-processing unit 14 and extracts pixels that are not too dark and not too bright, as proper-exposure pixels.

Next, the carotene-content calculating unit 23 reads the carotene content stored in the storage unit 20 and further calculates an average between the carotene content and the calculated average value of the fat image signal. Then, the calculated carotene-content average value is sent to the storage unit 20.

Here, when the difference between the carotene content read from the storage unit 20 and the calculated average value of the fat image signal is larger than a predetermined value, the carotene-content calculating unit 23 excludes the calculated average value of the fat image signal from a target to be used to calculate the average with respect to the carotene content read from the storage unit 20. When the calculated average value of the fat image signal is excluded from a target to be used to calculate an average value, because an average value is not calculated, the carotene content in the storage unit 20 is not updated, either.

The predetermined value is set large at the start of a surgery and is gradually reduced as the number of detections of exposed fat increases.

Furthermore, when the number of pixels to be used to calculate an average value is small, the carotene-content calculating unit 23 also excludes the calculated average value of the fat image signal from a target to be used to calculate an average with respect to the carotene content read from the storage unit 20, and thus, the carotene content in the storage unit 20 is not updated.

The correction unit 24 corrects the fat image signal generated in the fat-image generating unit 18 on the basis of the carotene content stored in the storage unit 20. Here, the correction unit 24 holds a corresponding map between a carotene value and a gain, multiplies the signal value of the fat image signal by a smaller gain as the carotene content is larger, and multiplies the signal value of the fat image signal by a larger gain as the carotene content is smaller.

The post-processing unit 25 performs, on the image signals input from the pre-processing unit 14, gradation conversion processing, color processing, and edge highlighting processing by using a gradation conversion coefficient, a color conversion coefficient, and an edge highlighting coefficient that are stored in advance in the control unit 17, thus generating a color image to be displayed on the image display unit 6.

The fat highlighting unit 26 performs highlighting processing for the fat image signal input from the post-processing unit 25 on the basis of the exposed-fat image corrected by the correction unit 24. Color highlighting of the image signals is performed for a region where the signal value of the corrected fat image signal is higher than the predetermined threshold. Furthermore, when an ON/OFF instruction signal for fat highlighting processing input from the external I/F unit 13 via the control unit 17 is set to OFF, the fat highlighting unit 26 does not perform the highlighting processing and sends the image signals input from the post-processing unit 25 to the image display unit 6 as they are. When the ON/OFF instruction signal is set to ON, the image signals obtained after the fat highlighting processing are sent to the image display unit 6.

The image display unit 6 is a display device that can display a moving image and is formed of a CRT or LCD monitor, for example.

The external I/F unit 13 is an interface with which an operator performs input and is provided with a highlighting processing button (not shown) for allowing an ON/OFF instruction for the fat highlighting processing to be issued. The operator operates the highlighting processing button, thereby making it possible to input, to the control unit 17, an ON/OFF instruction signal for the fat highlighting processing. The external I/F unit 13 is provided with a power switch for turning on/off the power and mode switching buttons for switching between capturing modes or various other modes.

The image processing method using the thus-configured living-body observation device 1 and image processing device 16 of this embodiment will be described below.

Figure 4:
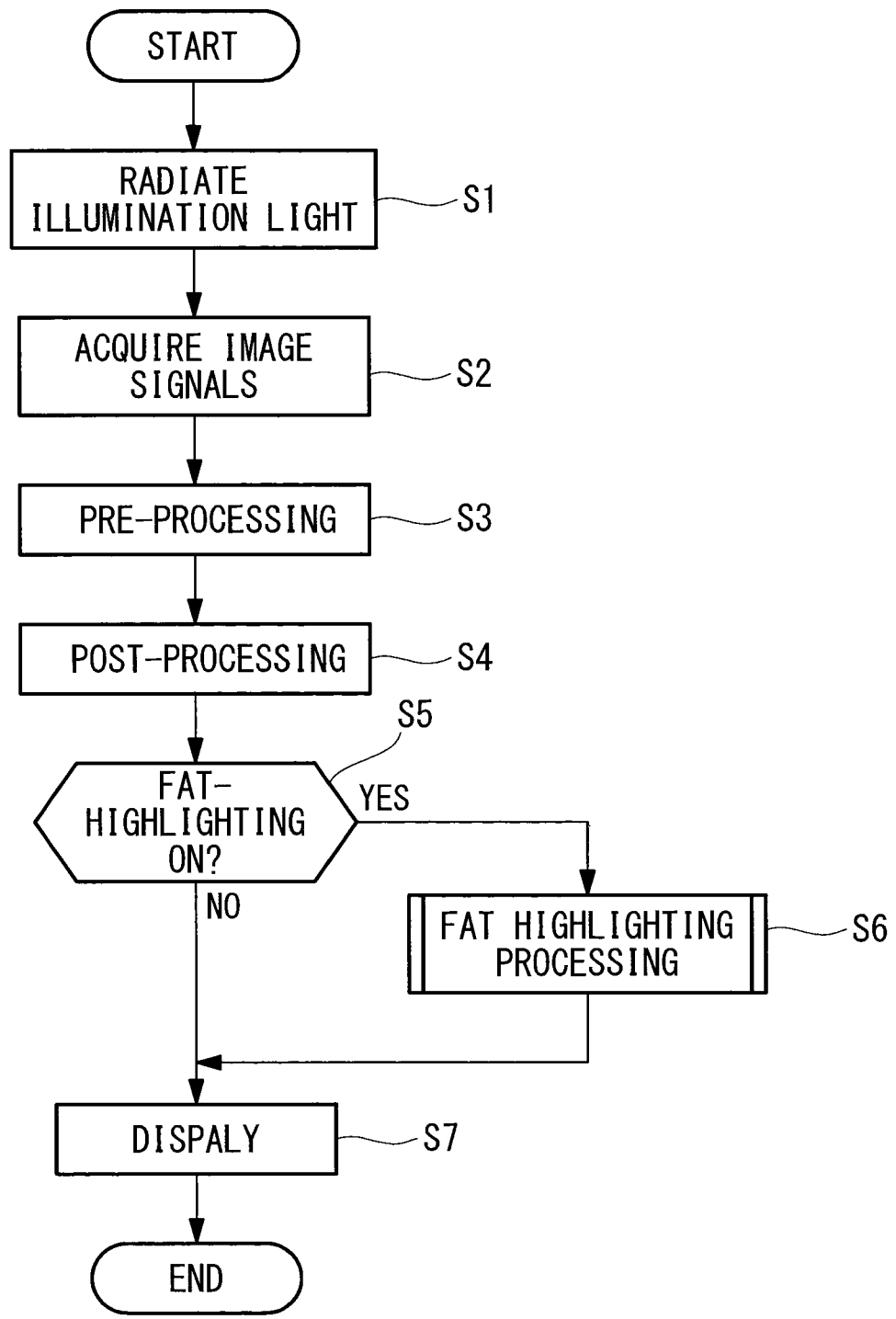
FIG. 4 is a flowchart showing an image processing method using the living-body observation device shown in FIG. 1.
Figure 5:
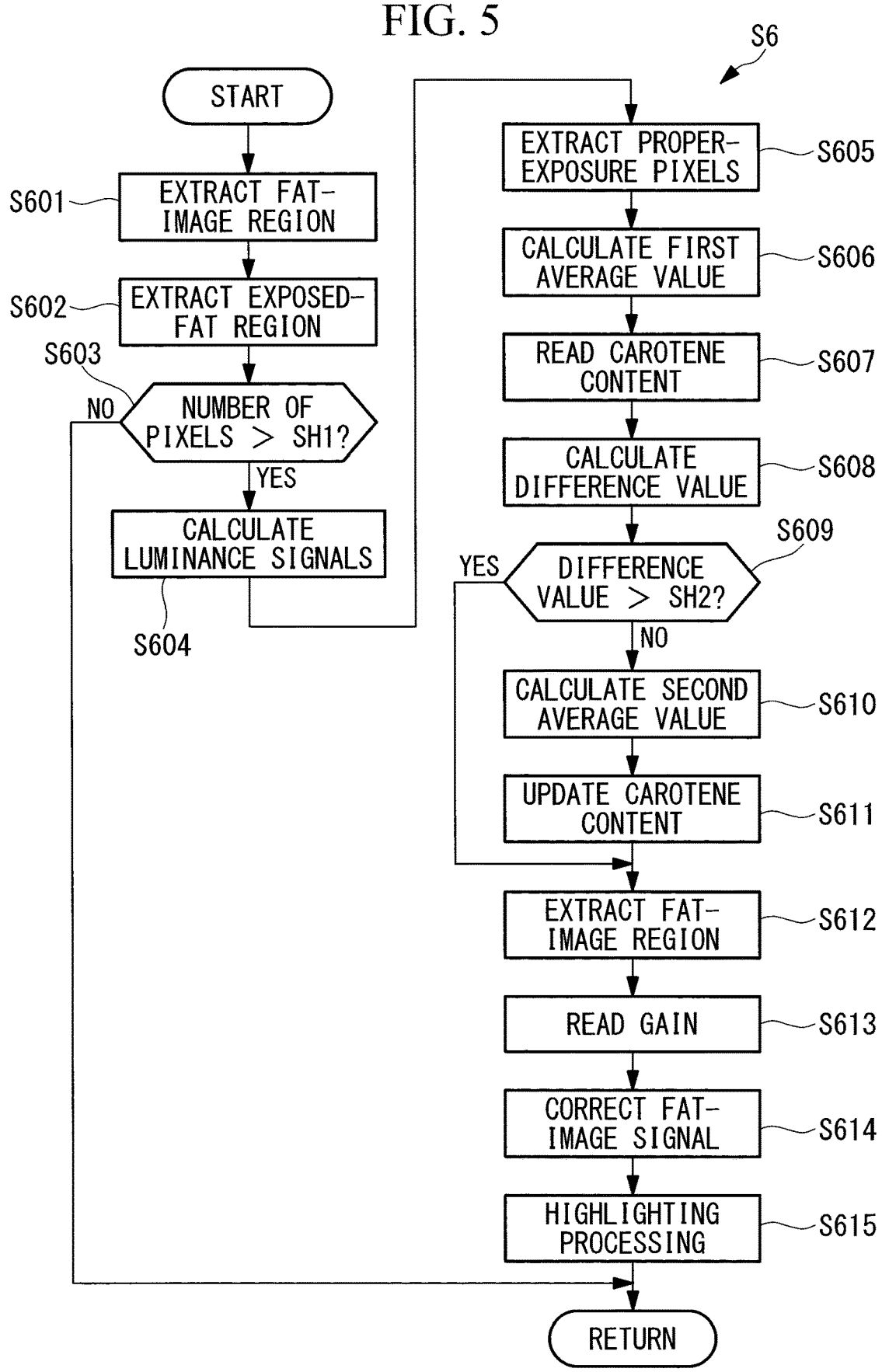
FIG. 5 is a flowchart showing, in detail, fat highlighting processing in the image processing method shown in FIG. 4.

In order to observe a living body by using the living-body observation device 1 of this embodiment, as shown in FIGS. 4 and 5, first, the insertion portion 2 is inserted into a body cavity, and, in a state in which the distal end of the insertion portion 2 is made to face an observation target site, the linear motion mechanism 22 is actuated through actuation of the control unit 17, to remove the short-wavelength cut filter 21 from the optical axis. In this state, white light with the wide wavelength band produced by the xenon lamp 11 is guided to the distal end of the insertion portion 2 via the light-guide cable 7 and is radiated onto living tissue (illumination-light radiating step S1).

The radiated white light is reflected at the surface of the living tissue, is collected by the objective lens 9, and is captured by the image acquisition device 10 (image-signal acquiring step S2). Because the image acquisition device 10, which is formed of the color CCD, is provided with color filters having transmittances for respective colors, image signals are acquired by pixels corresponding to the respective colors. The acquired image signals are subjected to demosaicing processing in the interpolation unit 15, thus being converted into three-channel image signals, and then, a white-light image is generated via the pre-processing unit 14, the post-processing unit 25, and the fat highlighting unit 26 and is displayed on the image display unit 6.

In the pre-processing unit 14, the three-channel image signals input from the interpolation unit 15 are subjected to pre-processing (for example, OB clamp processing, gain correction processing, and WB correction processing; pre-processing step S3) by using the OB clamp value, the gain correction value, and the WB coefficient value, which are stored in advance in the control unit 17. Furthermore, in the post-processing unit 25, the image signals obtained after the pre-processing input from the pre-processing unit 14 are subjected to post-processing (for example, gradation conversion processing, color processing, and edge highlighting processing; post-processing step S4) by using the gradation conversion coefficient, the color conversion coefficient, and the edge highlighting coefficient, which are stored in advance in the control unit 17. An ON/OFF instruction signal for the fat highlighting processing sent from the external I/F unit 13 is examined (fat-highlighting examining step S5). A white-light image to be displayed on the image display unit 6 is generated (display step S7).

Because the ON/OFF instruction signal for the fat highlighting processing sent from the external I/F unit 13 is set to OFF, the processing is not performed in the fat highlighting unit 26. This observation mode is referred to as a white-light observation mode.

In this white-light observation mode, the operator can observe the form of living tissue by means of the white-light image displayed on the image display unit 6.

When the operator changes the ON/OFF instruction signal of the fat highlighting processing to ON via the external I/F unit 13, the control unit 17 actuates the linear motion mechanism 22 to insert the short-wavelength cut filter 21 on the optical axis.

White light produced by the xenon lamp 11 is transmitted through the short-wavelength cut filter 21, which cuts the wavelength band that is equal to or shorter than 450 nm, and is guided to the distal end of the insertion portion 2 via the light-guide cable 7 and is irradiated onto living tissue (illumination-light radiating step S1). The radiated illumination light is reflected at the surface of the living tissue, is collected by the objective lens 9, and is captured by the image acquisition device 10 (image-signal acquiring step S2). This observation mode is referred to as a special-light observation mode.

Although image signals acquired by pixels corresponding to green and red of the image acquisition device 10 are the same as those acquired in the white-light observation mode, an image signal acquired by pixels corresponding to blue is a signal corresponding to a wavelength band included in the range from 450 nm to 500 nm, obtained after the wavelength band that is equal to or shorter than 450 nm is cut.

The acquired image signals are subjected to demosaicing processing in the interpolation unit 15, thus being converted into three-channel image signals, and then, the three-channel image signals are subjected to image processing in the image processing unit 16.

Specifically, the three-channel image signals input from the interpolation unit 15 to the image processing unit 16 are subjected to pre-processing in the pre-processing unit 14 (pre-processing step S3) and are input to the post-processing unit 25, the fat-image generating unit 18, and the carotene-content calculating unit 23. The post-processing performed in the post-processing unit 25 (post-processing step S4) is the same as that performed in the white-light observation mode. In the fat-image generating unit 18, a one-channel fat image signal is generated from the three-channel image signals processed in the pre-processing unit 14.

Compared with the wavelength band B0 from 400 nm to 450 nm, which is cut by the short-wavelength cut filter 21, the wavelength band B1 from 450 nm to 500 nm for blue in this special-light observation mode is a wavelength band in which the absorption by β-carotene is larger than the absorption by hemoglobin. Therefore, compared with an image acquired by radiating light in the wavelength band B0, an image acquired by radiating light in this wavelength band B1 is less affected by the absorption by blood and is largely affected by the absorption by fat. Thus, an image that better reflects the distribution of fat can be acquired.

Furthermore, the wavelength band of green is a wavelength band in which there is no absorption by β-carotene, and there is much absorption by hemoglobin. Therefore, it can be said that, in an image acquired by radiating light in this wavelength band, a low-luminance region indicates a region where blood exists irrespective of the presence of fat. In short, tissue containing much hemoglobin, such as blood and blood vessels, can be clearly displayed.

Furthermore, the wavelength band of red is a wavelength band in which there is no absorption by β-carotene or absorption by hemoglobin. Therefore, it can be said that an image acquired by radiating light in this wavelength band shows the luminance distribution based on the morphological characteristics of the living-body surface.

Then, after the post-processing in the post-processing unit 25 (post-processing step S4), an ON/OFF instruction signal for the processing fat highlighting processing is examined (fat-highlighting examining step S5). At this time, because the instruction signal is set to ON, the image highlighting processing is performed (image-highlighting processing step S6).

In the fat-image generating unit 18, on the basis of the three-channel image signals acquired in the special-light observation mode, a one-channel fat image signal whose signal value becomes higher as the carotene content is higher is generated (fat-image-region extracting step S601).

The fat image signal generated in the fat-image generating unit 18 is sent to the exposed-fat detecting unit 19, the carotene-content calculating unit 23, and the correction unit 24.

In the exposed-fat detecting unit 19, pixels having fat image signals whose values are equal to or higher than a predetermined threshold SH1 are extracted, thereby detecting an exposed-fat region where fat is exposed without being covered with other tissue (exposed-fat-region extracting step S602).

The coordinates of the pixels constituting the exposed-fat region detected in the exposed-fat detecting unit 19 are sent to the carotene-content calculating unit 23.

In the carotene-content calculating unit 23, first, it is judged whether the number of the pixels constituting the exposed-fat region sent from the exposed-fat detecting unit 19 is larger than the predetermined threshold SH1 (number-of-pixels judging step S603). If the number of the pixels constituting the exposed-fat region is equal to or less than the predetermined threshold SH1, the average value is not calculated. If the number of the pixels constituting the exposed-fat region is larger than the predetermined threshold SH1, luminance signals are calculated from the three-channel image signals sent from the pre-processing unit 14 (luminance-signal calculating step S604), and pixels that are not too dark and not too bright are extracted as proper-exposure pixels (proper-exposure-pixel extracting step S605). Then, the carotene-content calculating unit 23 calculates, from the fat image signal generated in the fat-image generating unit 18, the average value (first average value) of the fat image signal at the coordinates of the pixels that are detected as the exposed-fat region in the exposed-fat detecting unit 19 and that are extracted as the proper-exposure pixels (first-average-value calculating step S606).

Accordingly, in a case in which the amount of data is less because the exposed-fat region is narrow, or in a case in which improper-exposure pixels are contained, an unreliable first average value is prevented from being calculated, thus making it possible to improve the accuracy of calculation of the carotene content.

Furthermore, the carotene-content calculating unit 23 reads the value of the carotene content stored in the storage unit 20 (carotene-content reading step S607) and further calculates an average value (second average value) with respect to the first average value (second-average-value calculating step S610, fat-color-component detecting step). Then, the carotene-content calculating unit 23 sends the calculated second average value to the storage unit 20, thus updating, in the storage unit 20, the value of the carotene content stored therein (carotene-content updating step S611).

In this case, in the carotene-content calculating unit 23, the difference value between the calculated first average value and the carotene content stored in the storage unit 20 is calculated (difference-value calculating step S608), and it is judged whether the difference value is larger than a predetermined threshold SH2 (difference-value judging step S609). If the difference value is larger than the predetermined threshold SH2, calculation of the second average value (second-average-value calculating step S610) is not performed, updating of the carotene content in the storage unit 20 (carotene-content updating step S611) is not updated, either, and the flowchart advances to a fat-image-region extracting step S612, to be described later. Accordingly, it is possible to prevent the disadvantage that the carotene content in the storage unit 20 is updated by a carotene content that is calculated on the basis of unreliable data.

Furthermore, the above-described threshold SH2 is set large at the start of observation and is gradually reduced as the number of calculations increases; thus, as the observation progresses, even when the difference value is small, the first average value is excluded from a target to be used to calculate the second average value, thus making it possible to suppress fluctuations in the carotene content stored in the storage unit 20.

In the correction unit 24, the fat image signal detected in the fat-image generating unit 18 (fat-image-region extracting step S612) is corrected on the basis of the carotene content stored in the storage unit 20 (fat-image-signal correcting step S614, correcting step). The correction unit 24 reads the carotene content stored in the storage unit 20, reads the gain stored in association with the carotene content (gain reading step S613), and multiplies the fat image signal by the gain.

The gain is stored such that the smaller the value of the carotene content is, the larger the gain is, and the larger the value of the carotene content is, the smaller the gain is. Thus, even when the carotene content contained in fat varies between individuals, similar fat image signals can be output as if the fat is the same.

Then, in the fat highlighting unit 26, the three-channel image signals output from the post-processing unit 25 are subjected to highlighting processing on the basis of the corrected fat image signal output from the correction unit 24 (highlighting processing step S615). Specifically, a special-light image in which image-signal color highlighting has been performed for a region where the signal value of the corrected fat image signal is higher than the predetermined threshold SH1 is generated, is sent to the image display unit 6, and is displayed thereon (display step S7).

In this way, according to the image processing device 16, the living-body observation device 1, and the image processing method of this embodiment, there is an advantage that, even when the carotene content contained in fat varies between individuals, as if the fat is the same, similar color highlighting can be performed for a region that has a similar fat image signal, and to stabilize the ease of distinguishing fat.

Specifically, in a case in which fat looks strong yellow because the carotene content is high, the correction unit 24 performs correction so as to suppress the degree of highlighting to be performed in the fat highlighting unit 26, and, in a case in which fat looks whitish because the carotene content is low, the correction unit 24 performs correction so as to increase the degree of highlighting to be performed in the fat highlighting unit 26. Accordingly, there is an advantage that stable highlighted images can be acquired irrespective of the color of fat, so that nerves in the fat layer are prevented from being damaged during a surgery.

Note that, in this embodiment, although exposed fat is detected from image signals acquired in the special-light observation mode, instead of this, exposed fat may be detected from image signals acquired in the white-light observation mode.

The exposed fat is observed as a yellow subject having high saturation in a white-light image, due to the absorption characteristics of β-carotene. By using this, the exposed-fat detecting unit 19 performs exposed-fat detection processing.

In this case, the control unit 17 switches between the white-light observation mode and the special-light observation mode at predetermined timing. When an instruction signal indicating that the image signals obtained after preprocessing are of a white-light image is input from the control unit 17, the exposed-fat detecting unit 19 starts exposed-fat-region detection processing. When the detection processing is started, the image signals are converted into chromaticity coordinates, and pixels whose hue is yellow and whose saturation is higher than the predetermined threshold SH1 are detected as an exposed-fat region.

When an instruction signal indicating the special-light observation mode is input from the control unit 17, the carotene-content calculating unit 23 calculates, from the fat image signal generated on the basis of image signals acquired in the special-light observation mode, the carotene content of an exposed-fat region detected in the white-light observation mode immediately before. Then, the fat image signal is corrected by the correction unit 24, and fat highlighting processing is performed in the fat highlighting unit 26.

Furthermore, in this embodiment, a description has been given of a single frame image; however, the present invention can also be applied to image processing of a plurality of frame images.

In this case, a plurality of frame images are arrayed in the time order manner, the carotene-content average values in the respective frame images are further averaged, and the carotene-content average value in the plurality of frame images is output by the carotene-content calculating unit 23.

By doing so, the carotene contents detected in the plurality of frame images acquired in time series are averaged, thus making it possible to more reliably remove a noise component and to improve the reliability.

Furthermore, in this embodiment, although the exposed-fat detecting unit 19 automatically detects exposed fat in an image signal, instead of this, it is also possible to provide an exposed-fat-region specifying unit (not shown) with which an operator specifies an exposed-fat region in a white-light image displayed on the image display unit 6.

Furthermore, in this embodiment, although a description has been given of a case in which highlighting processing performed in the fat highlighting unit 26 is color highlighting, instead of this, it is also possible to perform highlighting processing in terms of brightness or structure.

Next, an image processing device 16, a living-body observation device 30, and an image processing method according to a second embodiment of the present invention will be described below with reference to the drawings.

In the following description of this embodiment, identical reference signs are assigned to portions having configurations common to those in the image processing device 16, the living-body observation device 1, and the image processing method of the above-described first embodiment, and a description thereof will be omitted.

Figure 6:
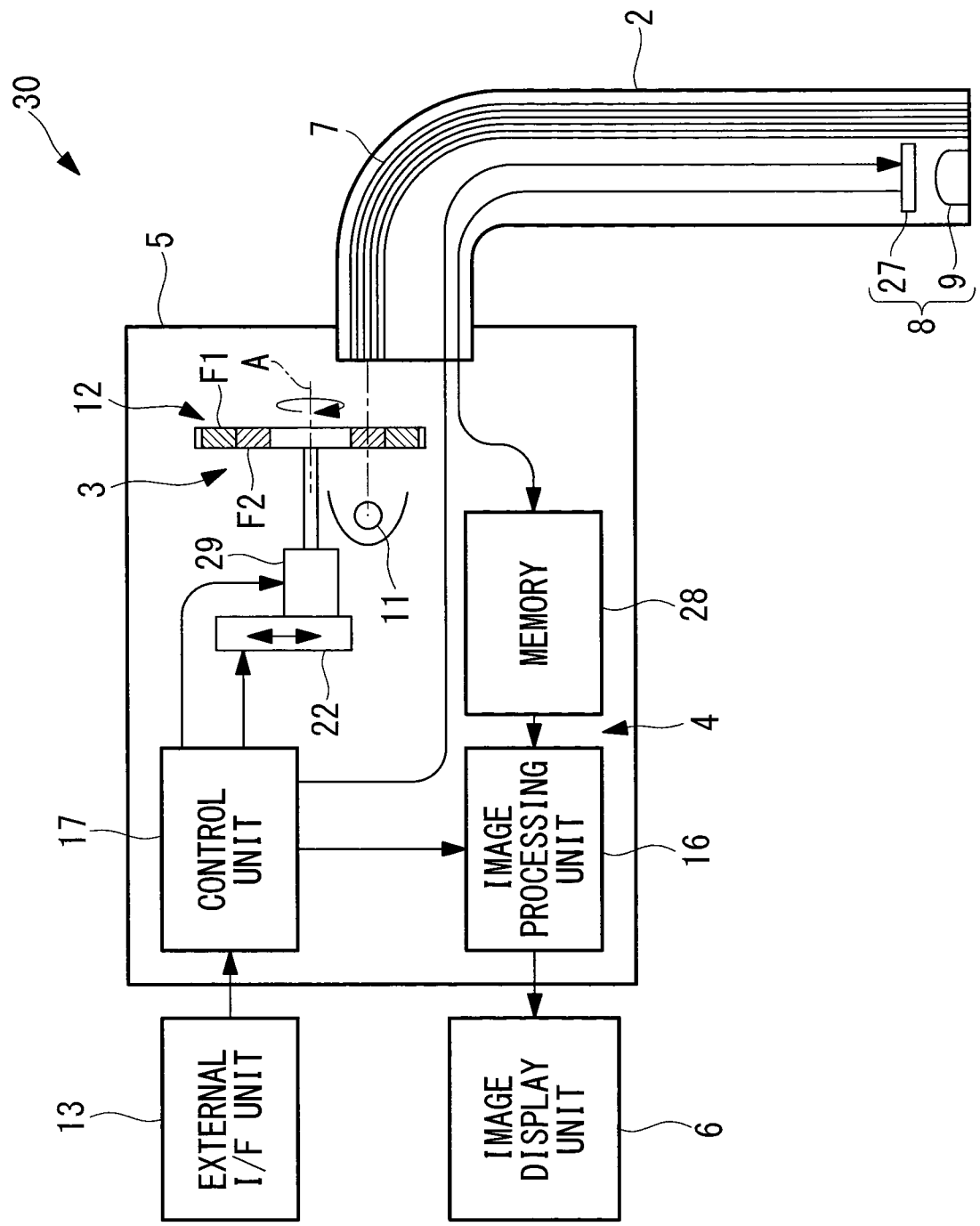
FIG. 6 is a schematic view showing the overall configuration of a living-body observation device according to a second embodiment of the present invention.

In the first embodiment, although a color CCD is adopted as the image acquisition device 10, and the three-channel image signals are simultaneously acquired, in this embodiment, instead of this, as shown in FIG. 6, a monochrome CCD is adopted as an image acquisition device 27, and a filter turret 12 that cuts out light having predetermined wavelengths from white light produced by the xenon lamp 11 and that makes the light sequentially pass therethrough in a time-division manner is disposed, instead of the short-wavelength cut filter 21.

Figure 7:
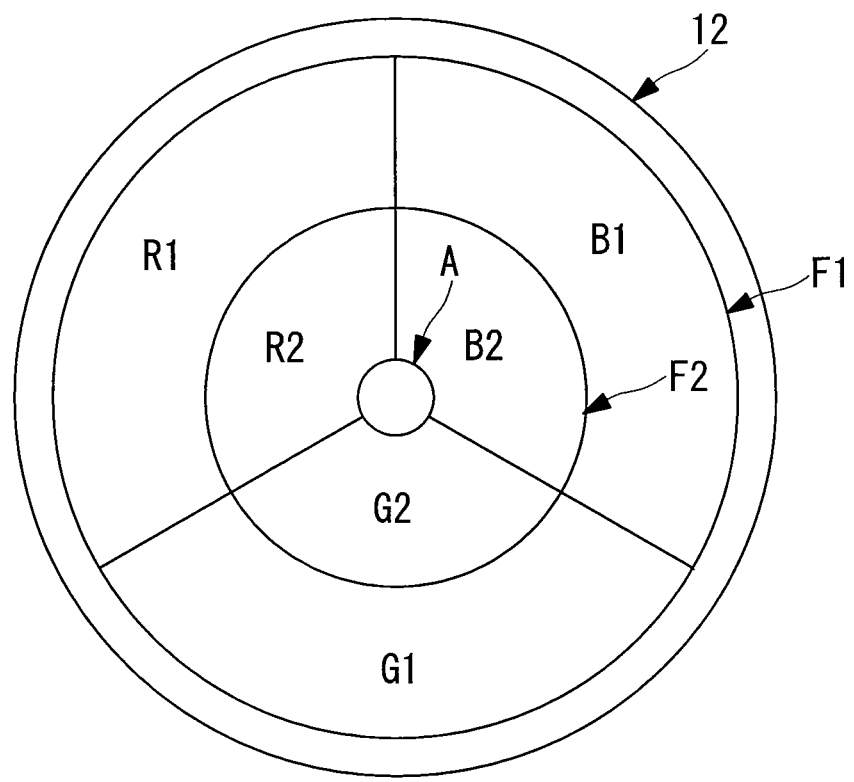
FIG. 7 is a front view showing arrangement of filters in a filter turret that is provided in the living-body observation device shown in FIG. 6.

As shown in FIG. 7, the filter turret 12 is provided with, for example, two types of filter groups that are disposed concentrically in radial directions with the center of rotation A serving as the center. In the figure, reference sign 29 denotes a motor.

Furthermore, the filter turret 12 is provided in a manner allowing it to be moved in a direction intersecting the optical axis of the xenon lamp 11 by the linear motion mechanism 22.

Accordingly, the filter turret 12 disposes one of the filter groups F1 and F2 on the optical axis of white light from the xenon lamp 11, thereby making it possible to emit light selected by the filter group F1 or F2, toward the insertion portion 2.

Figure 8A:
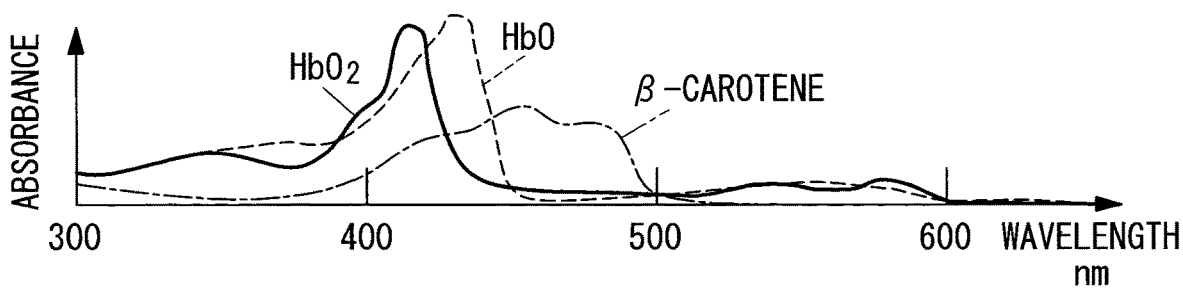
FIG. 8A is a view showing absorption characteristics of β-carotene and absorption characteristics of hemoglobin.
Figure 8B:
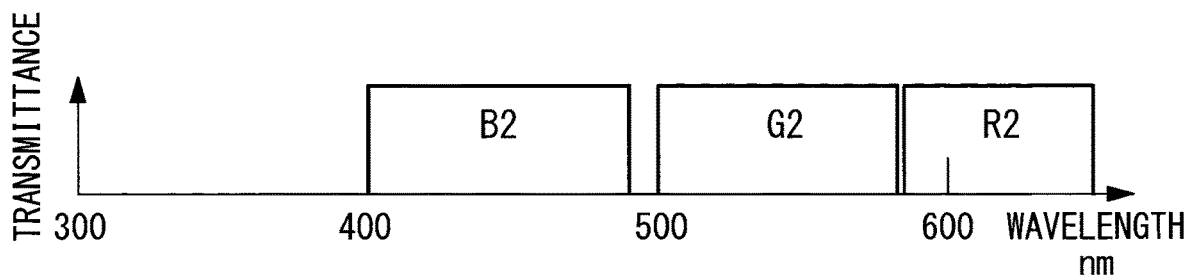
FIG. 8B is a view showing transmittance characteristics of filters used in a white-light observation mode in the living-body observation device shown in FIG. 7.
Figure 8C:
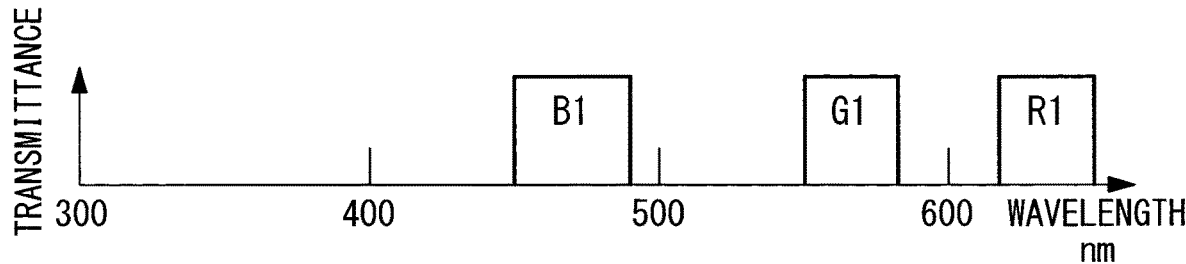
FIG. 8C is a view showing transmittance characteristics of filters used in a special-light observation mode in the living-body observation device shown in FIG. 7.

As shown in FIG. 8C, the first filter group F1 is configured by arranging, in a circumferential direction, filters B1, G1, and R1 having high transmittances for blue (B1: 450 nm to 480 nm), green (G1: 550 nm to 570 nm), and red (R1: 620 nm to 650 nm), among the wavelength bands of blue, green, and red.

As shown in FIG. 8B, the second filter group F2 is configured by arranging, in a circumferential direction, filters B2, G2, and R2 that transmit light in substantially-continuous wavelength bands of blue (B2: 400 nm to 490 nm), green (G2: 500 nm to 570 nm), and red (R2: 590 nm to 650 nm).

In the wavelength band of blue of the first filter group F1, compared with the wavelength band of blue of the second filter group F2, absorption by β-carotene is larger than absorption by hemoglobin; therefore, an image acquired by radiating light therein is less affected by the absorption by blood vessels and has much absorption by fat tissue. On the other hand, an image obtained by individually capturing reflected light of light transmitted through the filters B2, G2, and R2 in the second filter group F2, by giving the corresponding colors to acquired image signals, and by compositing the image signals becomes a white-light image.

Furthermore, in the wavelength band of green G1 of the first filter group F1, there is no absorption by β-carotene, and there is absorption by hemoglobin; thus, in an image acquired by radiating light therein, a low-intensity region indicates a region where blood exists, for example, a blood vessel.

Furthermore, in the wavelength band of red R1 of the first filter group F1, there is no absorption by β-carotene or absorption by hemoglobin; thus, an image acquired by radiating light therein shows morphological characteristics of the living-tissue surface.

The signal processing unit 4 is provided with a memory 28 that stores image signals acquired by the image acquisition device 27, for the respective wavelengths of radiated illumination light. The image processing unit 16 performs image processing for giving different colors to the image signals stored in the memory 28 and compositing the image signals.

Furthermore, the control unit 17 synchronizes the timing of capturing performed by the image acquisition device 27, the rotation of the filter turret 12, and the timing of image processing performed by the image processing unit 16.

In the thus-configured living-body observation device 30 of this embodiment, first, the second filter group F2 of the filter turret 12 is moved to a position where it is disposed on the optical axis of light from the xenon lamp 11, illumination light beams in the blue B2, the green G2, and the red R2 are sequentially radiated, and reflected light beams reflected at the subject when these illumination light beams are radiated thereonto are sequentially captured by the image acquisition device 27.

Pieces of image information corresponding to the illumination light beams of the respective colors are sequentially stored in the memory 28, and, when pieces of image information corresponding to the three types of illumination light, i.e., illumination light beams in the blue B2, the green G2, and the red R2, are obtained, they are sent from the memory 28 to the image processing unit 16. In the image processing unit 16, the respective types of image processing are performed in the pre-processing unit 14 and the post-processing unit 25, and, in the post-processing unit 25, the colors of the illumination light beams radiated when the pieces of image information are acquired are given to the pieces of image information, and the pieces of image information are composited. Accordingly, a white-light image is generated, and the generated white-light image is sent to the image display unit 6 via the fat highlighting unit 26 and is displayed thereon.

In the white-light image, for example, in a region where a blood vessel exists, the blood vessel is displayed in red because there is absorption in the wavelength bands of the blue B2 and the green G2. Furthermore, in a region where fat exists, the fat is displayed in yellow because there is absorption in the wavelength band of the blue B2. However, if fat tissue is extremely thin, the color of a blood vessel in an organ that is located at a rear side of the fat tissue is transmitted therethrough, thus making it difficult to recognize the existence of the fat tissue.

Then, in such a case, the first filter group F1 of the filter turret 12 is moved to a position where it is disposed on the optical axis of light from the xenon lamp 11, illumination light beams in the blue B1, the green G1, and the red R1 are sequentially radiated, and reflected light beams reflected at the subject when these illumination light beams are radiated are sequentially captured by the image acquisition device 27.

Then, as in capturing of a white-light image, pieces of image information corresponding to the illumination light beams of the respective colors are sequentially stored in the memory 28, and, when pieces of image information corresponding to the three types of illumination light, i.e., illumination light beams in the blue B1, the green G1, and the red R1, are obtained, the three-channel image signals are sent to the image processing unit 16.

The image processing performed in the image processing unit 16 is the same as that in the first embodiment.

In this way, even in the method for sequentially obtaining three-channel image signals by using the monochrome CCD 27, as in the method for simultaneously obtaining three-channel image signals by using the color CCD 10, because a fat image signal is corrected according to the carotene content calculated from a special-light image, there is an advantage that fat can be displayed in a distinguishable manner even if the color of fat varies between individuals.

Figure 9:
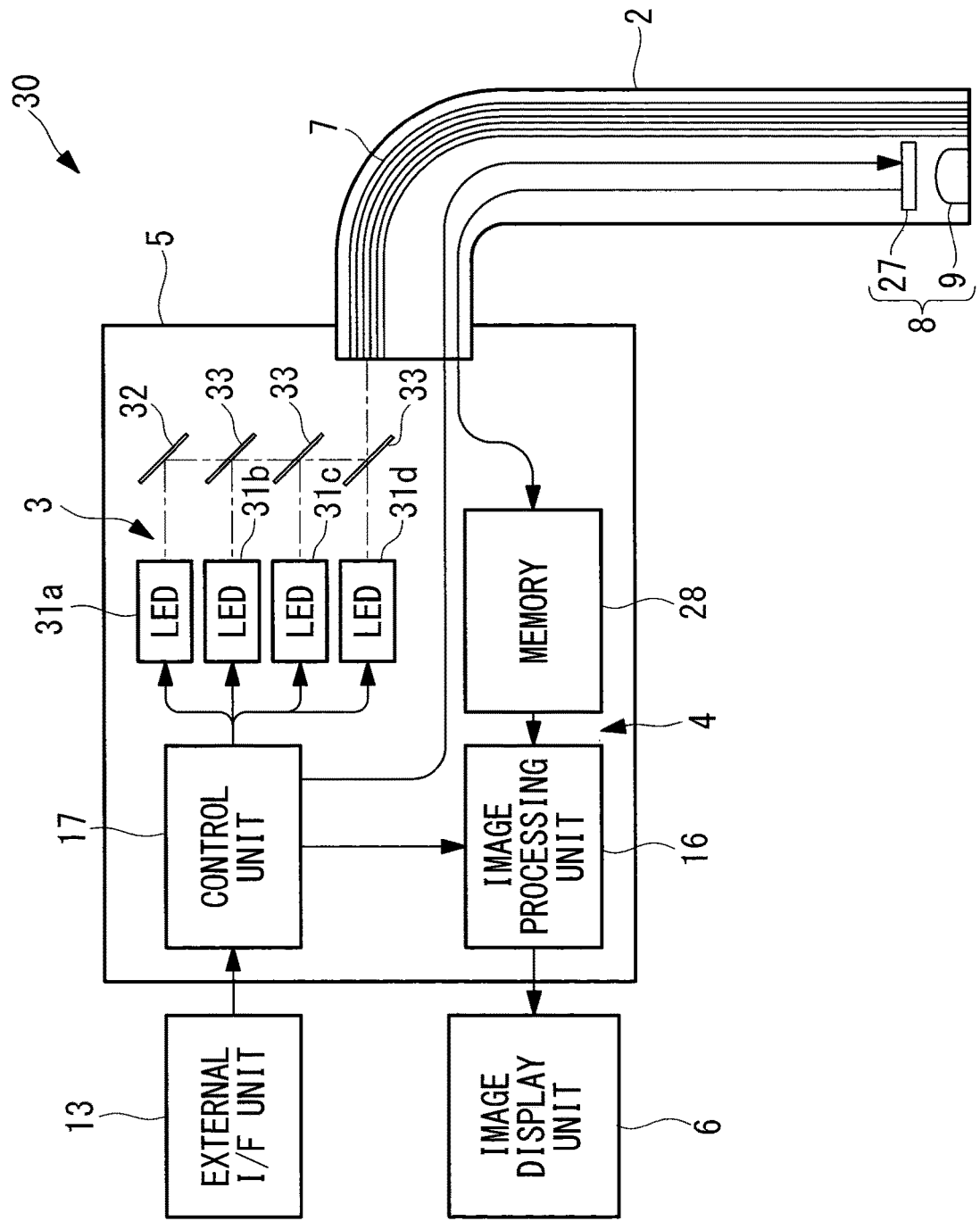
FIG. 9 is a schematic view showing the overall configuration of a first modification of the living-body observation device shown in FIG. 6.

Note that, in this embodiment, although the light source unit 3 sequentially emits light beams in different wavelength bands by means of the xenon lamp 11 and the filter turret 12, instead of this, as shown in FIG. 9, it is also possible to provide a plurality of light-emitting diodes (LEDs) 31a, 31b, 31c, and 31d that emit light beams in different wavelength bands such that light beams therefrom can be made to enter the same light-guide cable 7 by means of a mirror 32 and dichroic mirrors 33.

Figure 10A:
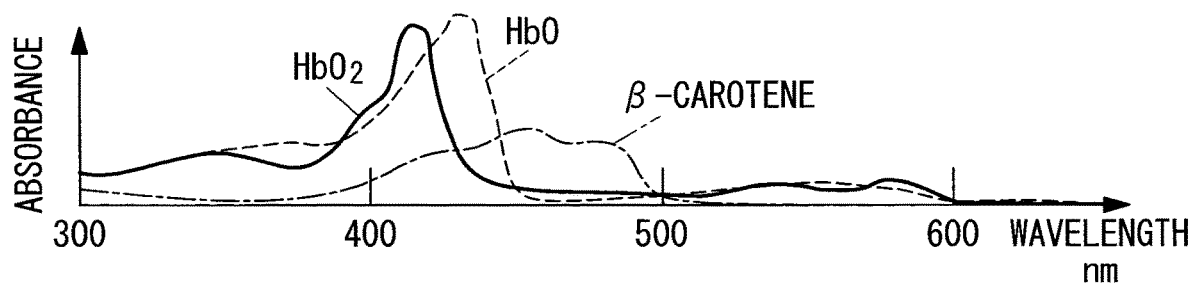
FIG. 10A is a view showing absorption characteristics of β-carotene and absorption characteristics of hemoglobin.
Figure 10B:
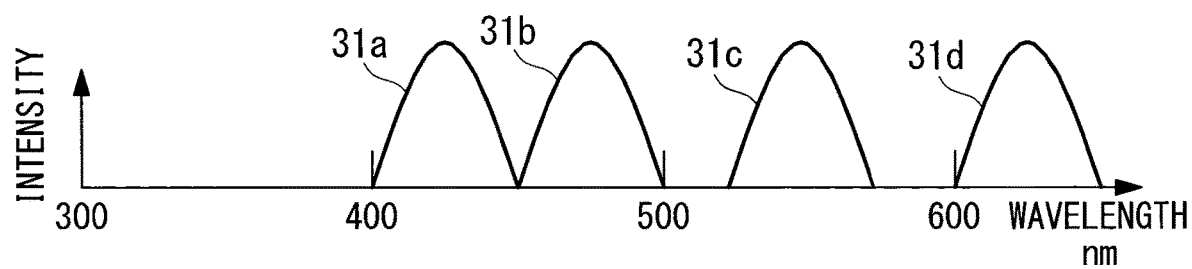
FIG. 10B is a view showing light-intensity characteristics of LEDs used in a white-light observation mode in the living-body observation device shown in FIG. 9.
Figure 10C:
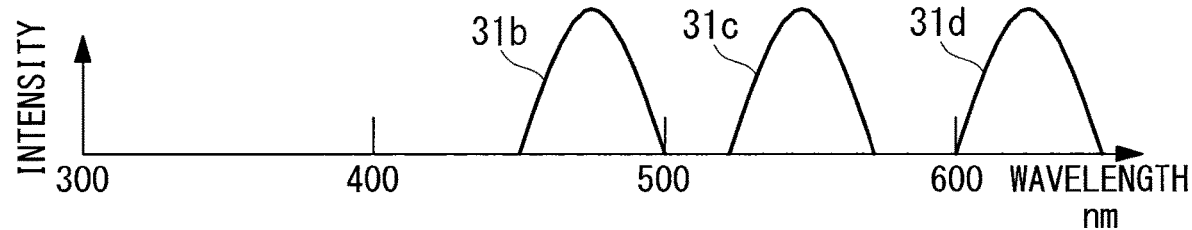
FIG. 10C is a view showing light-intensity characteristics of LEDs used in a special-light observation mode in the living-body observation device shown in FIG. 9.

In the example shown in FIG. 9, the four light-emitting diodes 31a, 31b, 31c, and 31d for the wavelength bands from 400 nm to 450 nm, from 450 nm to 500 nm, from 520 nm to 570 nm, and from 600 nm to 650 nm are prepared. Then, in the white-light observation mode, as shown in FIG. 10B, light beams from the light-emitting diodes 31a and 31b, for the wavelength band from 400 nm to 500 nm, are used as blue illumination light, light from the light-emitting diode 31c, for the wavelength band from 520 nm to 570 nm, is used as green illumination light, and light from the light-emitting diode 31d, for the wavelength band from 600 nm to 650 nm, is used as red illumination light. On the other hand, in the special-light observation mode, as shown in FIG. 10C, the light-emitting diode 31b, for the wavelength band from 450 nm to 500 nm, is used as blue illumination light.

Figure 11:
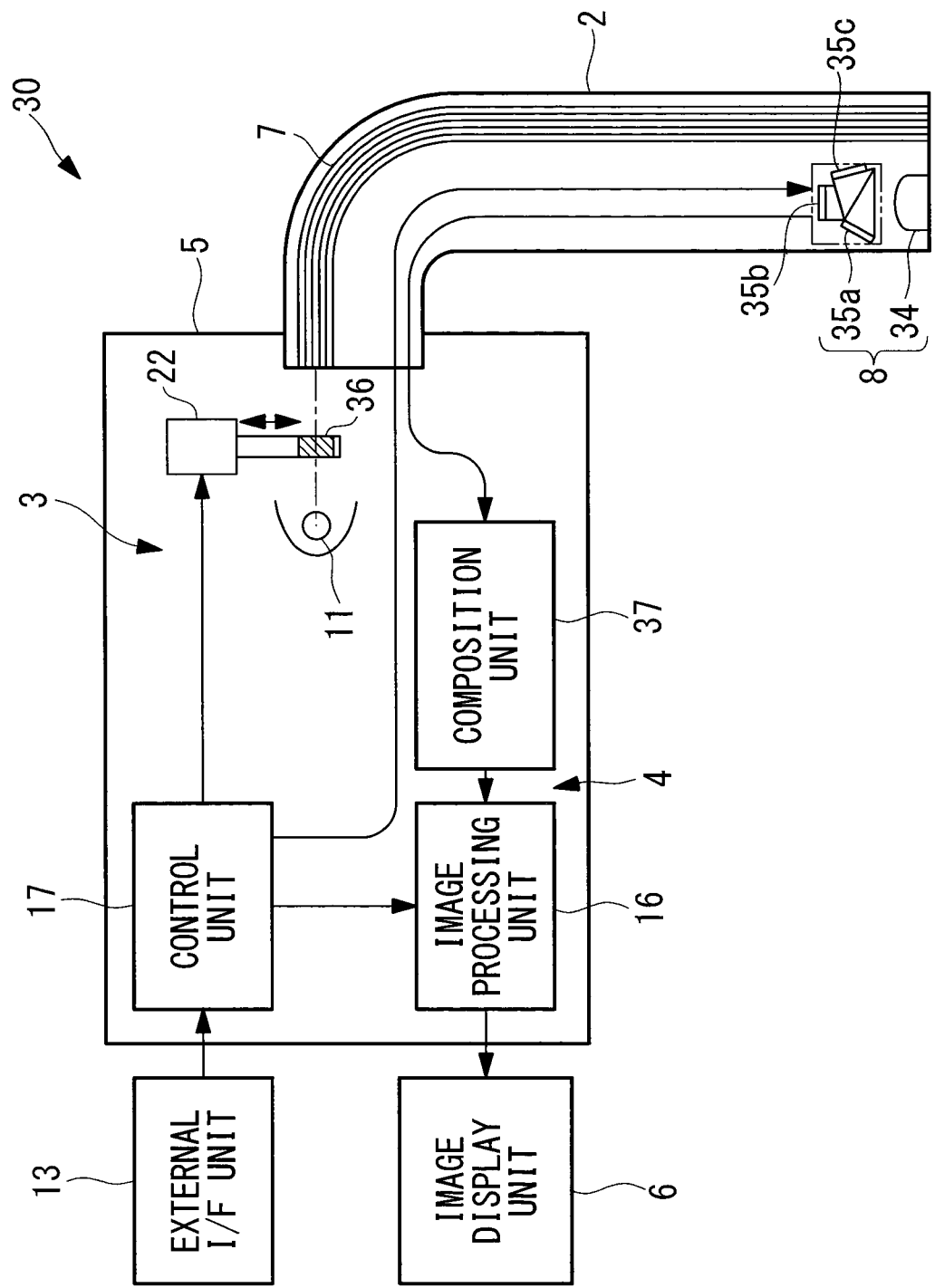
FIG. 11 is a schematic view showing the overall configuration of a second modification of the living-body observation device shown in FIG. 6.

Furthermore, as shown in FIG. 11, it is also possible to adopt a 3CCD system that is provided with: a color-separation prism 34 that disperses reflected light returning from the subject for wavelength bands; and three monochrome CCDs 35a, 35b, and 35c that capture light beams in the respective wavelength bands.

The color-separation prism 34 disperses reflected light from the subject for the respective wavelength bands according to the transmittance characteristics shown in FIG. 12B.

Figure 12D:
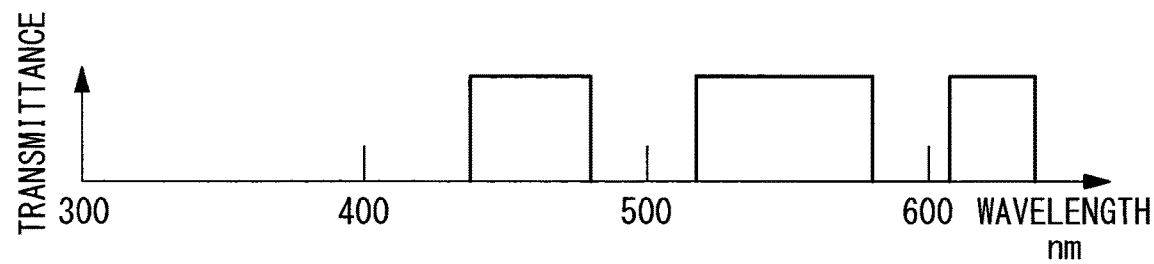
FIG. 12D is a view showing transmittance characteristics of filters used in a special-light observation mode in the living-body observation device shown in FIG. 11.

In this case, a filter 36 that can be inserted on or removed from the optical axis of light from the xenon lamp 11 by the linear motion mechanism 22 is provided instead of the filter turret 12. As shown in FIG. 12D, the filter 36 transmits light in three desired wavelength bands and blocks light in the other wavelength bands.

Then, the filter 36 is removed from the optical axis in the white-light observation mode, and the filter 36 is inserted on the optical axis in the special-light observation mode. Then, the images acquired by the monochrome CCDs 35a, 35b, and 35c are formed into three-channel image signals in a composition unit 37, and the three-channel image signals are input to the image processing unit 16. By doing so, as in the above-described living-body observation device 30, in the special-light observation mode, thin fat that exists on the surface of an organ or other tissue, such as connective tissue, can be displayed while being highlighted.

Furthermore, it is also possible to provide a magnification switching unit (not shown) that switches the observation magnification, and the observation mode may be switched to the special-light observation mode when the observation magnification is switched to a high magnification and may be switched to the white-light observation mode when the observation magnification is switched to a low magnification. During observation at a high magnification, the special-light observation mode is selected, thereby making it possible to perform precise processing while confirming the boundary between fat and the other tissue. During observation at a low magnification, the white-light observation mode is selected, thereby making it possible to perform broad observation of the whole site to be treated.

Furthermore, the living-body observation devices 1 and 30 of the present invention are not limited to an endoscope and can be applied to a device for broadly observing a living body, such as a living-body observation device used in a robotic surgery.

The inventor has arrived at the following aspects of the present invention.

An aspect of the present invention is an image processing device including: a fat-image-region extracting unit that extracts a fat-image region that is a region where fat exists in a living-tissue image; a fat-color-component detecting unit that detects a fat-color-component amount that determines a color of fat, from the fat-image region extracted by the fat-image-region extracting unit; and a correction unit that corrects intensity of signals of the fat-image region extracted by the fat-image-region extracting unit, on the basis of the fat-color-component amount detected by the fat-color-component detecting unit.

According to this aspect, the fat-image-region extracting unit extracts a fat-image region from an input living-tissue image, and the fat-color-component detecting unit detects a fat-color-component amount that determines the color of fat. The color of fat existing in a living body varies between individuals due to differences in race or in eating habits. For example, in a person who has a high amount of β-carotene contained in fat, the fat looks strong yellow; in contrast, in a person who has a low amount of β-carotene contained in fat, the fat looks whitish. Therefore, the correction unit corrects the intensity of the signals of the fat-image region on the basis of the detected fat-color-component amount, thereby making it possible to stably distinguish fat irrespective of individual differences and to prevent damage to nerves that surround a target organ.

Furthermore, according to another aspect, the present invention provides an image processing device including: a fat-image-region extracting unit that extracts a fat-image region that is a region where fat exists in a living-tissue image; an exposed-fat-region specifying unit that allows an operator to specify an exposed-fat region, in the living-tissue image, where fat is exposed without being covered with another tissue; a fat-color-component detecting unit that detects a fat-color-component amount that determines a color of fat, from the exposed-fat region specified through the exposed-fat-region specifying unit; and a correction unit that corrects intensity of signals of the fat-image region extracted by the fat-image-region extracting unit, on the basis of the fat-color-component amount detected by the fat-color-component detecting unit.

According to this aspect, the fat-image-region extracting unit extracts a fat-image region from an input living-tissue image, and the exposed-fat-region specifying unit allows an operator to specify an exposed-fat region in the input living-tissue image. Then, the fat-color-component detecting unit detects a fat-color-component amount that determines the color of fat, from the specified exposed-fat region. The correction unit corrects intensity of the signal of the fat-image region on the basis of the detected fat-color-component amount, thereby making it possible to stably distinguish fat irrespective of individual differences and to prevent damage to nerves that surround a target organ. Because the fat-color-component amount is detected from the exposed-fat region, it is possible to stably detect a fat-color-component amount without being affected by the other tissues and to stably distinguish fat.

The above-described aspect may further include an exposed-fat detecting unit that detects an exposed-fat region where fat is exposed without being covered with another tissue, from the fat-image region extracted by the fat-image-region extracting unit, wherein the fat-color-component detecting unit may detect the fat-color-component amount on the basis of the exposed-fat region detected by the exposed-fat detecting unit.

By doing so, the exposed-fat region is automatically detected from the fat-image region extracted by the fat-image-region extracting unit, thereby making it possible to stably detect a fat-color-component amount without being affected by the other tissue and to stably distinguish fat.

Furthermore, in the above-described aspect, the fat-color-component detecting unit may extract proper-exposure pixels from the exposed-fat region detected by the exposed-fat detecting unit and may detect the fat-color-component amount on the basis of the extracted proper-exposure pixels.

By doing so, because, in the exposed-fat region detected by the exposed-fat detecting unit, proper-exposure pixels are used as fat-color-component-amount detection targets, it is possible to accurately detect the fat-color-component amount on the basis of the exposed-fat region from which a dark portion and a bright portion in the living-body image are excluded.

Furthermore, the above-described aspect may further include a storage unit that stores a reference value for the fat-color-component amount, wherein the fat-color-component detecting unit may output an average value between the fat-color-component amounts for respective pixels in the fat-image region and the reference value and may update the reference value stored in the storage unit to be the output average value.

By doing so, the fat-color-component amounts detected, from a fat-image region that is composed of a plurality of pixels, for the respective pixels are averaged with respect to the reference value stored in the storage unit, and the resultant is output. The fat-color-component amounts are averaged, thereby making it possible to remove a noise component to calculate a stable fat-color-component amount, and are averaged with respect to the reference value, thereby making it possible to use the accumulated past data, thus improving the accuracy of detection of the fat-color-component amount. The storage unit stores, as an initial value, an appropriate reference value or a reference value that is experimentally or empirically calculated, and the reference value is updated each time a new fat-color-component amount is detected, thereby making it possible to accumulate data.

Furthermore, the above-described aspect may further include a storage unit that stores a reference value for the fat-color-component amount, wherein the fat-color-component detecting unit may output, when the exposed-fat region detected by the exposed-fat detecting unit exists over an area having more than a predetermined number of pixels, an average value between the fat-color-component amounts for respective pixels in the fat-image region and the reference value and may update the reference value stored in the storage unit to be the output average value.

By doing so, when exposed fat is less in the living-tissue image, there is a high possibility that the reliability of a fat color component to be detected becomes low; thus, this is excluded, thereby making it possible to detect a highly-reliable fat-color-component amount and to use the thus-detected highly-reliable fat-color-component amount for the next image processing, as well.

Furthermore, in the above-described aspect, the living-tissue image may be provided with a plurality of frame images arranged in a time order manner; and the fat-color-component detecting unit may further output an average value of the fat-color-component amounts in the plurality of frame images.

By doing so, because fat-color-component amounts detected in the plurality of frame images acquired in time series are averaged, a noise component can be removed more reliably.

Furthermore, in the above-described aspect, when difference between the fat-color-component amount detected by the fat-color-component detecting unit and the reference value stored in the storage unit is larger than a predetermined threshold, this fat-color-component amount may be excluded from a target to be used in calculating the average value.

By doing so, when the difference from the reference value stored in the storage unit is large, the average value with respect to the reference value fluctuates greatly; thus, the fat-color-component amount is excluded as an error value, thereby making it possible to stably detect the fat-component amount.

Furthermore, in the above-described aspect, the predetermined threshold may be set so as to become gradually smaller in response to the number of calculations of the average value.

By doing so, even when the difference from the reference value becomes small as the number of detections of the fat-color-component amount increases, the number of exclusions as an error value increases; thus, the fluctuation in the detected fat-color-component amount is reduced, thereby making it possible to perform more stable detection.

Furthermore, in the above-described aspect, the fat-color-component detecting unit may detect carotene content contained in fat.

By doing so, the carotene content is detected as a fat color component that determines the color of fat, thereby making it possible to more-reliably and stably distinguish fat irrespective of individual differences and to prevent damage to nerves that surround a target organ.

Furthermore, in the above-described aspect, the living-tissue image may be a special-light image that is obtained by capturing reflected light in a wavelength band included in the range from 450 nm to 500 nm.

By doing so, in a blue wavelength band included in the range from 450 nm to 500 nm, compared with the other blue wavelength band, absorption by β-carotene is larger than absorption by hemoglobin. Thus, a special-light image acquired by capturing reflected light in this wavelength band is less affected by the absorption by blood vessels and has much absorption by fat tissue. Therefore, the carotene content can be accurately detected from this special-light image.

Furthermore, in the above-described aspect, as the living-tissue image, a white-light image and a special-light image that is obtained by capturing reflected light in a wavelength band included in the range from 450 nm to 500 nm may be input; the fat-image-region extracting unit may extract the fat-image region on the basis of the white-light image; and the fat-color-component detecting unit may detect the fat-color-component amount on the basis of the special-light image.

By doing so, an exposed-fat region can be easily extracted on the basis of the white-light image used for living-body observation, and the fat-color-component amount in the extracted exposed-fat region can be accurately detected on the basis of the special-light image.

Furthermore, the above-described aspect may further include a fat highlighting unit that performs, for the fat-image region of which the signal intensity has been corrected by the correction unit, highlighting processing for allowing it to be distinguished from surrounding tissue, and generates an image in which the fat-image region has been highlighted.

By doing so, the fat highlighting unit distinguishes a fat-image region from the surrounding tissue, thereby making it possible to acquire a stable highlighted image irrespective of the color of fat.

Furthermore, another aspect of the present invention is a living-body observation device including: a radiation unit that radiates illumination light onto living tissue; an image acquisition unit that acquires a living-tissue image by capturing, within reflected light reflected at the living tissue onto which the illumination light has been radiated by the radiation unit, reflected light in a wavelength band in which absorption characteristics of β-carotene are higher than absorption characteristics of hemoglobin; the above-described image processing device that processes the living-tissue image acquired by the image acquisition unit; and a display unit that displays an image generated by the fat highlighting unit.

According to this aspect, illumination light is radiated onto living tissue from the radiation unit, and reflected light reflected at the living tissue is captured by the image acquisition unit. The image acquisition unit captures reflected light in a wavelength band in which absorption characteristics of β-carotene are larger than absorption characteristics of hemoglobin; thus, it is possible to acquire a living-tissue image that is less affected by the existence of a blood vessel and that is affected by the existence of fat. Then, the carotene content can be accurately detected from a fat-image region extracted from the thus-acquired living-tissue image, and the signal intensity of the fat-image region can be corrected on the basis of the detected carotene content. Accordingly, it is possible to stably distinguish fat irrespective of individual differences and to prevent damage to nerves that surround a target organ.

Furthermore, another aspect of the present invention is a living-body observation device including: a radiation unit that radiates illumination light onto living tissue; an image acquisition unit that acquires a living-tissue image by capturing reflected light reflected at the living tissue onto which the illumination light has been radiated by the radiation unit; and the above-described image processing device.

In the above-described aspect, the image acquisition unit may acquire a white-light image of living tissue and a special-light image thereof that is obtained by capturing reflected light in a wavelength band included in the range from 450 nm to 500 nm; the exposed-fat-region specifying unit may cause an operator to specify the exposed-fat region in the white-light image; and the fat-color-component detecting unit may detect the fat-color-component amount on the basis of the special-light image.

Furthermore, another aspect of the present invention is a fat-image-region extracting step of extracting a fat-image region that is a region where fat exists in a living-tissue image; a fat-color-component detecting step of detecting a fat-color-component amount that determines a color of fat, from the fat-image region extracted in the fat-image-region extracting step; and a correcting step of correcting intensity of signals of the fat-image region extracted in the fat-image-region extracting step, on the basis of the fat-color-component amount detected in the fat-color-component detecting step.

According to the aforementioned aspects, an advantageous effect is afforded in that fat can be stably distinguished irrespective of individual differences, thereby making it possible to prevent damage to nerves that surround a target organ.

REFERENCE SIGNS LIST 1, 30 living-body observation device
3 light source unit (radiation unit)
6 image display unit (display unit)
8 capturing optical system (image acquisition unit)
16 image processing device (image processing unit)
18 fat-image generating unit (fat-image-region extracting unit)
19 exposed-fat detecting unit
20 storage unit
23 carotene-content calculating unit (fat-color-component detecting unit)
24 correction unit
26 fat highlighting unit
S601 fat-image-region extracting step
S610 second-average-value calculating step (fat-color-component detecting step)
S614 fat-image-signal correcting step (correcting step)

The invention claimed is:

1. An image processing device comprising:
a processor; and
a storage storing a program,
wherein the processor is configured by the program to at least:
obtain a one-channel fat image in a wavelength range channel in which fat is represented;
detect, in the one-channel fat image, an exposed-fat region where the fat is exposed and not covered by another tissue;
detect a fat-color-component amount from pixels which constitute the exposed-fat region and which constitute a sub-region of the one-channel fat image; and
correct intensity of signals of the one-channel fat image extracted, on the basis of the fat-color-component amount detected.

2. The image processing device according to claim 1, wherein the processor is configured by the program to:
extract proper-exposure pixels having luminance within a predetermined luminance range from the exposed-fat region detected; and
detect the fat-color-component amount on the basis of the extracted proper-exposure pixels.

3. The image processing device according to claim 1, wherein the storage stores a reference value for the fat-color-component amount, and
wherein the processor is configured by the program to:
output an average value between the fat-color-component amount and the reference value; and
update the reference value stored in the storage to be the average value output.

4. The image processing device according to claim 1, wherein the storage stores a reference value for the fat-color-component amount, and
wherein the processor is configured by the program to:
determine whether the exposed-fat region detected exists over an area having more than a predetermined number of pixels;
output, in response to determining that the exposed-fat region detected exists over an area having more than the predetermined number of pixels, an average value between the fat-color-component amount and the reference value; and
update the reference value stored in the storage to be the average value output.

5. The image processing device according to claim 3, wherein the processor is configured to:
obtain a plurality of the one-channel fat image arranged in a time order manner; and
detect the exposed-fat region where the fat is exposed and not covered by another tissue in each of the plurality of the one-channel fat image;
detect the fat-color-component amount from pixels which constitute the exposed-fat region and which constitute the sub-region of the each of the plurality of the one-channel fat image;
determine an average value of the fat-color-component amounts detected from the pixels which constitute the exposed-fat region and which constitute the sub-region of the each of the plurality of the one-channel fate image; and
correct the intensity of signals of one of the plurality of the one-channel fat image, on the basis of the average value of the fat-color-component amounts.

6. The image processing device according to claim 3, wherein the processor is configured by the program to:
determine whether a difference between the fat-color-component amount detected and the reference value stored in the storage is larger than a predetermined threshold; and
exclude, in response to determining that the difference between the fat-color-component amount detected and the reference value stored in the storage is larger than the predetermined threshold, the fat-color-component amount from being a target to be used in calculating the average value.

7. An image processing device according to claim 6, wherein the predetermined threshold is set so as to become gradually smaller in response to the number of calculations of the average value.

8. The image processing device according to claim 1, wherein the processor is configured by the program to:
detect carotene content contained in fat; and
detect the fat-color-component amount based on the carotene content detected.

9. An image processing device according to claim 1, wherein the one-channel fat image is a special-light image that is obtained by capturing reflected light in a wavelength range channel from 450 nm to 500 nm.

10. The image processing device according to claim 1, wherein the processor is configured by the program to generate an image in which the fat is highlighted to be distinguished from surrounding tissue, based on the one-channel fat image of which the signal intensity has been corrected.

11. A living-body observation device comprising:
an image sensor configured to acquire a living-tissue image by capturing, within reflected light reflected from a living tissue onto which illumination light has been radiated toward the living tissue, reflected light in a wavelength band in which absorption characteristics of β-carotene are higher than absorption characteristics of hemoglobin;

the image processing device according to claim 10, that processes the one-channel fat image derived from the living-tissue image acquired by the image sensor; and a display configured to display the image, generated by the image processing device, in which the fat is highlighted to be distinguished from the surrounding tissue.

12. An image processing method comprising:

obtaining, by a processor configured by a program, a one-channel fat image in a wavelength range channel in which fat is represented;

detecting, by the processor configured by the program, an exposed-fat region where the fat is exposed and not covered by another tissue;

detecting, by the processor configured by the program, a fat-color-component amount from pixels which constitute the exposed-fat region and which constitute a sub-region of the one-channel fat image; and correcting, by the processor configured by the program, intensity of signals of the one-channel fat image obtained, on the basis of the fat-color-component amount detected.

* * * * *